(12) United States Patent
Miller et al.

(10) Patent No.: US 10,363,347 B2
(45) Date of Patent: Jul. 30, 2019

(54) BREAST PUMP SYSTEM

(71) Applicants: Jared Miller, Chesterfield, MO (US); Samantha Rudolph, Chesterfield, MO (US)

(72) Inventors: Jared Miller, Chesterfield, MO (US); Samantha Rudolph, Chesterfield, MO (US)

(*) Notice: Subject to any disclaimer, the term of this patent is extended or adjusted under 35 U.S.C. 154(b) by 556 days.

(21) Appl. No.: 15/149,525

(22) Filed: May 9, 2016

(65) Prior Publication Data

US 2016/0325031 A1   Nov. 10, 2016

Related U.S. Application Data (60) Provisional application No. 62/158,303, filed on May 7, 2015.

(51) Int. Cl.
| | | |
|---|---|---|
| *A61M 1/06* | (2006.01) | |
| *A61M 39/24* | (2006.01) | |
| *A61M 39/22* | (2006.01) | |

(52) U.S. Cl.
CPC .............. *A61M 1/062* (2014.02); *A61M 1/06* (2013.01); *A61M 1/066* (2014.02); *A61M 39/223* (2013.01); *A61M 39/24* (2013.01); *A61M 2039/2433* (2013.01); *A61M 2205/3393* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/8206* (2013.01)

(58) Field of Classification Search
CPC ......... A61M 1/06; A61M 1/062; A61M 1/064
See application file for complete search history.

(56) References Cited

U.S. PATENT DOCUMENTS

| | | |
|---|---|---|
| 603,564 A | 5/1898 | Hoover |
| 3,822,703 A | 7/1974 | Davisson |
| 4,607,596 A | 8/1986 | Whittlestone |
| 4,680,028 A | 7/1987 | Stuart |
| 4,772,262 A | 9/1988 | Grant |
| 4,964,851 A | 10/1990 | Larsson |
| 5,295,957 A | 3/1994 | Aida |
| 5,415,632 A | 5/1995 | Samson |
| 5,542,921 A | 8/1996 | Meyers |
| 5,897,580 A | 4/1999 | Silver |
| 5,954,690 A | 9/1999 | Larsson |
| 6,004,288 A | 12/1999 | Hochstedler |
| 6,213,840 B1 | 4/2001 | Han |

(Continued)

*Primary Examiner* — Jason E Flick
*Assistant Examiner* — Courtney B Fredrickson
(74) *Attorney, Agent, or Firm* — Linda L Lewis; CreatiVenture Law, LLC (57) ABSTRACT

A breast pump system having a suction tubing, a milk tubing, a pump, a three way vent valve, a milk bottle, an isolation valve and a breast shield, wherein the first end of the suction tubing and the first end of the milk tubing are fluidly connected to the pump; wherein the second end of the suction tubing and the second end of the milk tubing are fluidly connected to the breast shield; wherein the three way vent valve is fluidly connected between the pump and the breast shield on the suction tubing; wherein the milk bottle is fluidly connected on the milk tubing between the breast shield and the pump; and wherein the isolation valve is connected on the milk tubing between the milk bottle and the pump.

10 Claims, 9 Drawing Sheets

(56) References Cited

U.S. PATENT DOCUMENTS

| | | |
|---|---|---|
| 6,379,327 B2 | 4/2002 | Lundy |
| 6,383,164 B1 | 5/2002 | Johansen |
| 6,500,143 B2 | 12/2002 | Suh |
| 7,758,540 B2 | 7/2010 | Yamashita |
| 8,137,153 B2 | 3/2012 | Bell |
| 8,398,584 B2 | 3/2013 | Britto |
| 8,500,679 B2 | 8/2013 | Holshouser |
| 8,529,501 B2 | 9/2013 | Wach |
| 8,900,182 B2 | 12/2014 | Britto |
| 2001/0044593 A1 | 11/2001 | Lundy |
| 2003/0191433 A1 | 10/2003 | Printiss |
| 2004/0127845 A1 | 7/2004 | Renz |
| 2005/0020971 A1 | 1/2005 | McKendry |
| 2007/0161330 A1 | 7/2007 | Whitehead |
| 2011/0071466 A1 | 3/2011 | Silver |
| 2014/0243766 A1 | 8/2014 | Martuch |
| 2014/0288466 A1 | 9/2014 | Alvarez |
| 2015/0065994 A1* | 3/2015 | Fridman .............. A61M 1/06 604/514 |

* cited by examiner

BREAST PUMP SYSTEM

CROSS-REFERENCE TO RELATED APPLICATIONS

This application claims the benefit of provisional patent application 62/158,303 filed May 7, 2015, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to a breast pump system, having a low volume and low noise pumping configuration to pump and store breast milk, where the storage of breast milk and positioning of the pump are remote from the breast.

Related Art

Prior art pump systems are limited to either a knob or up/down buttons for control of the unit. Some systems have dual controls, one for suction and one for speed, but many have just a single control. They typically have either no memory device, or are limited to a single preset setting. Prior art pump systems do not correlate pump settings (suction, cycle time) to amount of milk produced, comfort level, or any other quantifiable values. Prior art systems on the market store the expressed milk in a vessel that is directly connected to the bottom of the breast shield. The means that the user effectively has bottles hanging from her breasts, which does not allow pumping to be done discreetly. This is extremely awkward for the user. A further complaint is that prior art breast shields are made of hard plastic and are uncomfortable. None of the prior art devices below do what the present invention does.

A complaint about prior art pumps is that they are noisy and make a pulsed mechanical sound. The larger the pump, the greater the noise created. The present invention has a configuration that provides a low volume pumping system that allows a smaller pump to be used, which will create less noise. Additionally, the present invention stores milk and positions the pump remote from the breast.

Examples of known prior art devices are described in the references listed below, which are hereby incorporated by reference. U.S. Pat. Nos. 5,616,125, 7,833,190, U.S. Application 2012/0,277,728 and U.S. Application 2006/0270,973 have breast pumps that have the milk pass through the pump. This is undesirable, since the pump now has to be cleaned with each use. U.S. Pat. No. 6,379,327 uses gravity and not suction to collect the milk, and can easily be upset by bending over or lying down. U.S. Pat. No. 6,440,100 has a single vacuum line that is also used to collect the milk. Milk can collect in the pump, so that the pump needs to be cleaned with every use. None of the above references disclose the claimed breast pump system with a low-volume pumping configuration with the milk container and the pump remote from the breast.

SUMMARY OF THE INVENTION

The present invention relates to an improved breast pump system comprising an improved pump that has reduced noise, a power source, a breast shield, a milk collector bottle, and a microprocessor attached to the pump and milk collector bottle for receiving and processing data regarding pump settings and milk volume.

The present invention further relates to an improved breast shield made of a soft plastic or silicone polymer and configured to resemble a baby's mouth as it nurses.

The present invention is a configuration that provides a low volume pumping system that allows a smaller pump to be used, which will create less noise. The pump is configured for continuous pumping which further decreases noise from switching on and off. Additionally, the present invention allows storage of milk and positioning of the pump remote from the breast.

The breast pump system comprises a suction tubing, a milk tubing, a pump, a three way vent valve, a milk bottle, an isolation valve and a breast shield, wherein the suction tubing has a first and second end and the milk tubing has a first and second end; wherein the first end of the suction tubing and the first end of the milk tubing are fluidly connected to the pump; wherein the second end of the suction tubing and the second end of the milk tubing are fluidly connected to the breast shield; wherein the three way vent valve is fluidly connected between the pump and the breast shield on the suction tubing; wherein the milk bottle is fluidly connected on the milk tubing between the breast shield and the pump; and wherein the isolation valve is connected on the milk tubing between the milk bottle and the pump.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
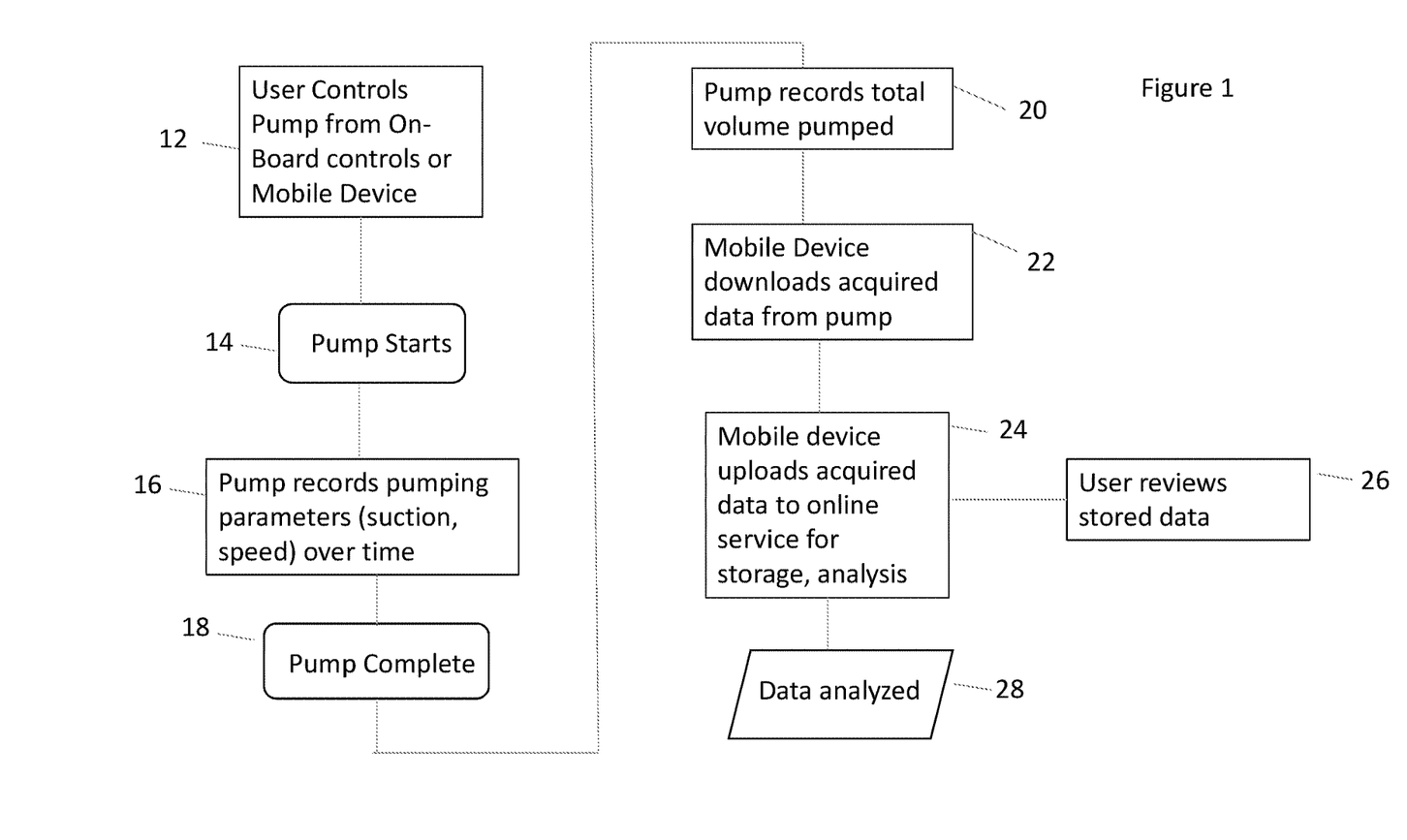
FIG. 1 is a flow diagram of the present breast pump system being used.

The flow diagram of FIG. 1 shows step 12 as controlling the breast pump system by use of a mobile devices, such as iPads or smart phones, or by controls on the device itself. In step 14, the pump starts pumping, and in step 16, pump parameters, such as the amount of suction produced and the speed of pumping is recorded. In step 18, the pumping is completed and stopped. In step 20, the pump system records the total volume of milk pumped and stored. In step 22, the mobile device downloads data from the pump. In step 24, the mobile device uploads the data to an online service that stores and analyses the data. In step 26, the breast pump user can review the data that is stored, or in step 28 the data that has been uploaded is analyzed.

Figure 2:
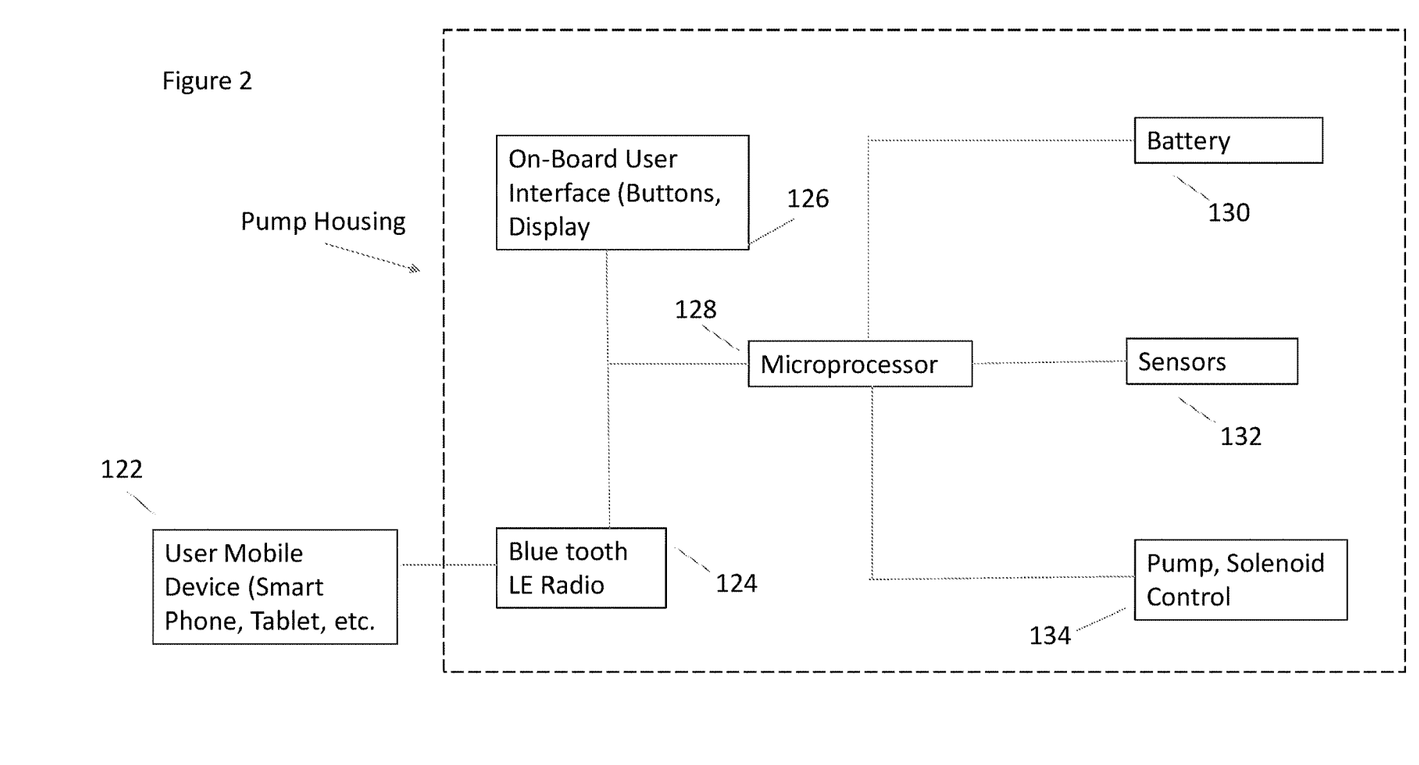
FIG. 2 is a block diagram of an embodiment of the present breast pump system.

The block diagram of FIG. 2 is an embodiment of the present breast pump system. In the pump housing is the on-board user interface 126 which is connected to the microprocessor 128 and a Bluetooth LE radio. Also connected to the microprocessor is the battery 130 power supply, the sensors 132 and the pump and solenoid valve control 134.

Figure 3A:
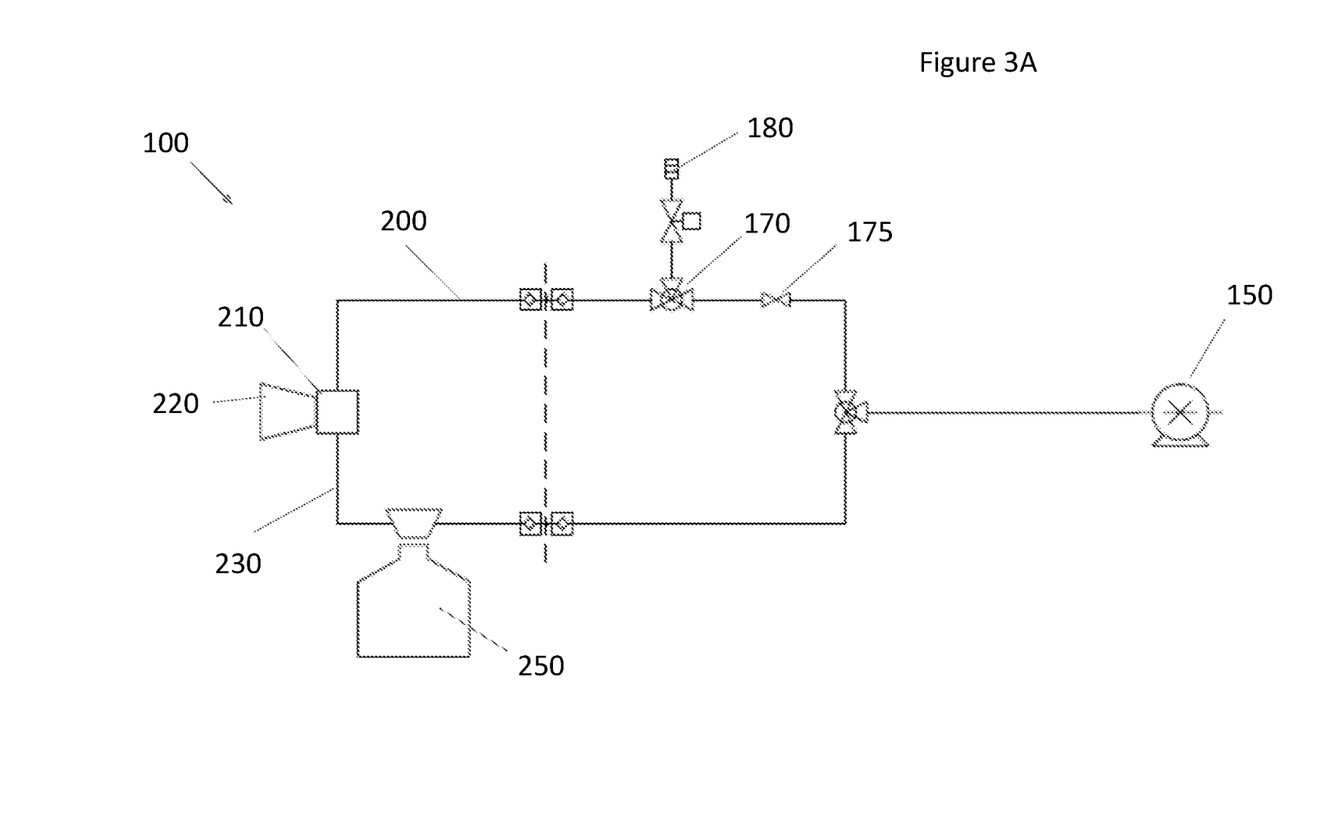
FIG. 3A is a first schematic of an embodiment of the present breast pump system.
Figure 3B:
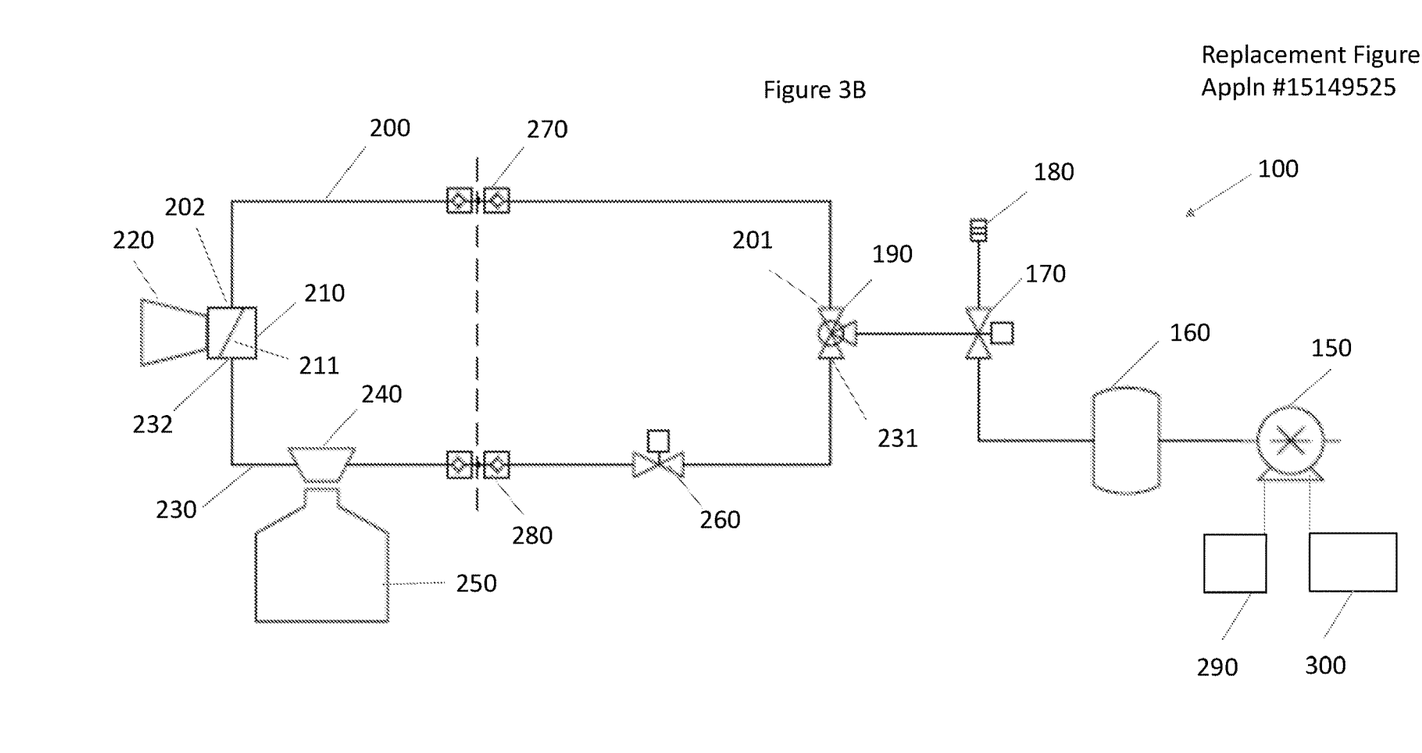
FIG. 3B is a second schematic of an embodiment of the present breast pump system.
Figure 7:
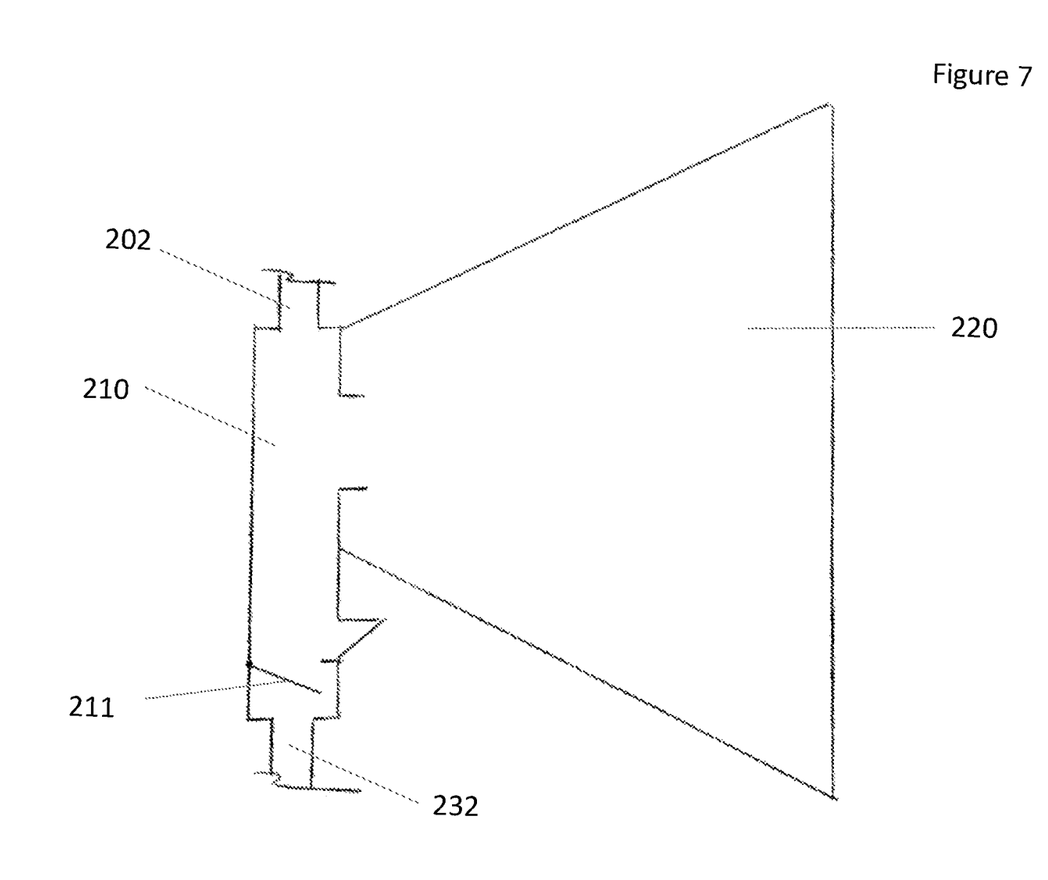
FIG. 7 is a cutaway side perspective drawing of the suction and milk separator device of the present invention.

In the diagrams of FIGS. 3A, 3B and 7, an embodiment of the breast pump system 100 has a vacuum pump 150 attached to a power source 300 and a microprocessor 290. Fluidly attached to the suction of the pump 150 is a vacuum cylinder 160. Fluidly attached to the vacuum cylinder is a vent valve 170. In a preferred embodiment, the vent valve 170 is a solenoid valve. The vent valve 170 can be a 3-way vent valve 170, as in FIG. 3B, or a 2-way vent valve 185 with a check valve 175, as in FIG. 3A. Also attached to the vent valve 170 is a vent 180 with an optional silencer and a manifold 190. In a preferred embodiment, the manifold is a 3-way connector having three attachment ports, wherein one of the attachment ports is fluidly attached to the vent 170. Fluidly attached to the second of the attachment ports is suction tubing 200 having a first end 201 and a second end 202. The first end 201 is attached to the manifold, which is fluidly attached to the pump. As is shown in FIG. 7, the second end 202 is fluidly attached to the suction and milk separator device 210. Fluidly attached to a third of the three attachments is milk tubing 230, where the milk tubing has a first end 231 and a second end 232. The first end 231 is fluidly attached to the manifold 190 at the third attachment port. Fluidly attached to the second end 232 is the suction and milk separator device 210. The suction and milk separator device 210 has three ports. The second ends 202 and 232 are attached to two ports, and the breast shield 220 is attached to the third. Preferably, the separator device has a check valve function to block flow of the suction to the milk tubing 230. In a preferred embodiment, this check valve is a diaphragm 211 on the second end 232. Between the first and second ends 231 and 232 is the milk bottle 250 with an optional lid 240. Positioned between the milk bottle and the manifold 190 is an isolation valve 260, which maintains vacuum in the milk bottle. In a preferred embodiment, the isolation valve is a solenoid valve. Fluidly attached to suction tubing 200 and milk tubing 230 is the breast shield 220, which is attached to the suction and milk separator device 210. The breast shield is molded out of flexible, soft material so that as suction is applied, the shield can comfortably conform to the shape of the breast.

Optionally, the suction tubing 200 and the milk tubing 230 can have connectors 270 and 280, respectively. This allows the breast shield 220 and the milk bottle 250 to be disconnected from the rest of the device for cleaning. In a preferred embodiment, the remainder of the device 100 that is disconnected is enclosed in a pump housing (not shown) for convenience.

Further optionally, a second breast shield (not shown) can be fluidly attached to the milk tubing and the suction tubing, so that both breasts can be pumped at the same time.

Figure 4:
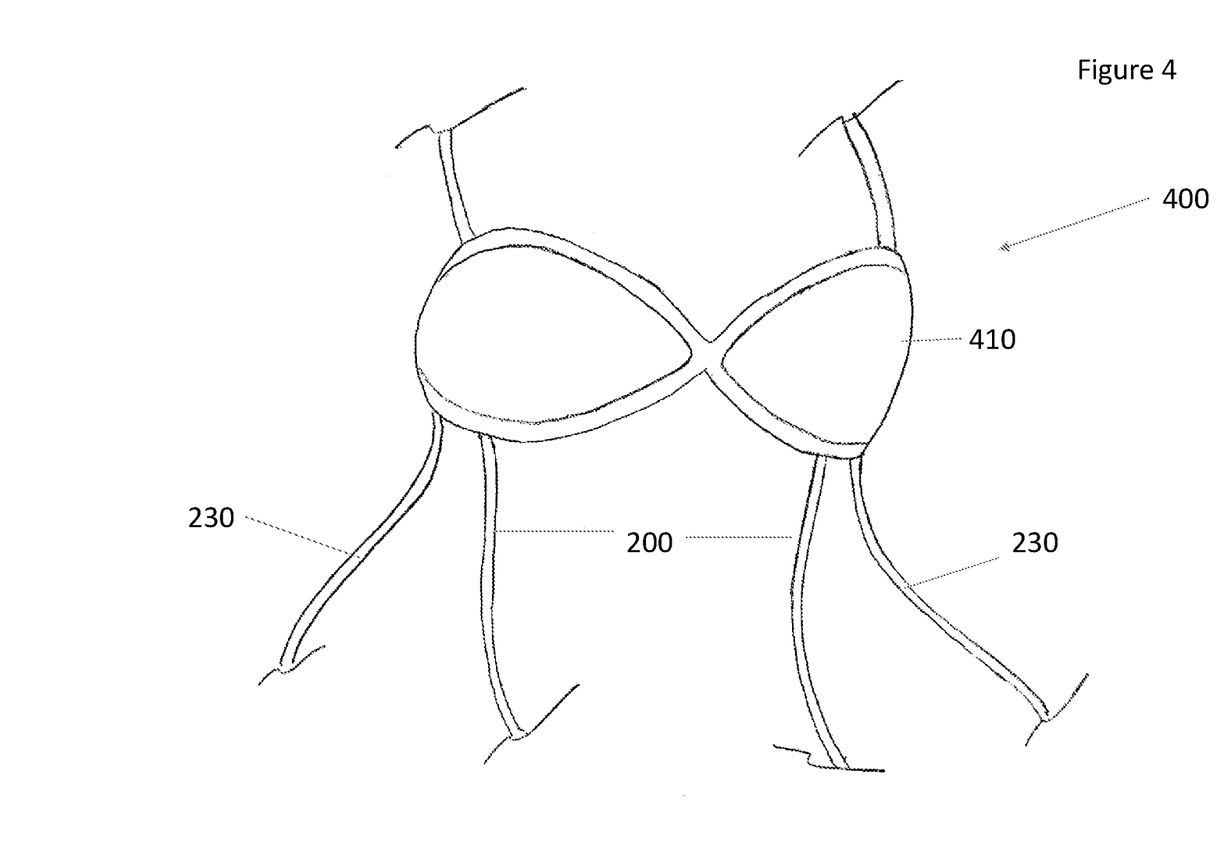
FIG. 4 is a front perspective drawing of a nursing bra of the present invention.
Figure 5:
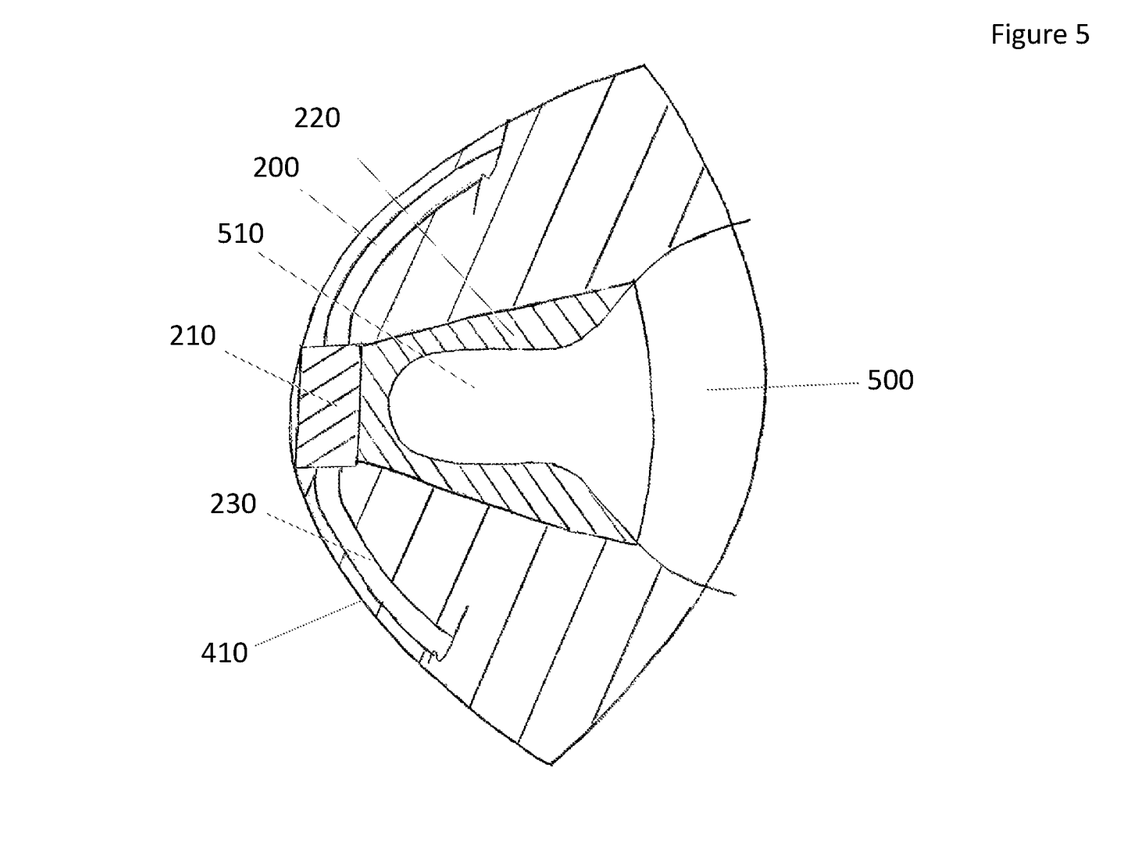
FIG. 5 is a cutaway side perspective drawing of the nursing bra of the present invention engaged with a breast.
Figure 6:
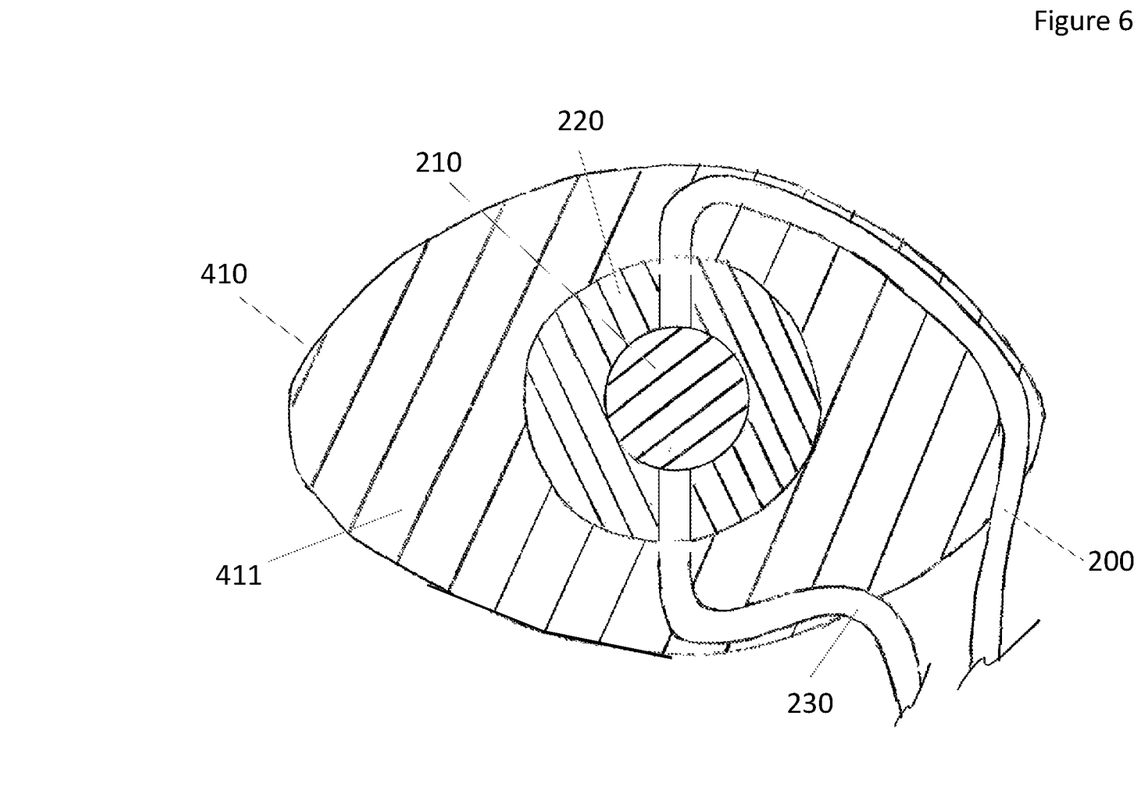
FIG. 6 is rear cutaway perspective drawing of the nursing bra of the present invention.

FIG. 4 shows an embodiment of a nursing bra 400 that has removable bra cups 410, as well as milk tubing 230 and suction tubing 200. FIG. 5 shows a side cutaway view of the breast shield 220 and the bra cups 410 applied to a breast 500 and nipples 510. The suction and milk separator device 210 is connected to the milk tubing 230 and the suction tubing 200. FIG. 6 shows a rear cutaway of the assembled bra cup 410, the removable breast pad 411, the breast shield 220 and the suction and milk separator device 210 with the milk tubing 230 and the suction tubing 200 attached.

Method of Operation: Three Cycles

1. Pumping:
The 3-way vent solenoid 170 is closed to the vent 180, and is open and connects fluidly to the manifold 190 and to the vacuum pump 150, and suction is applied to the suction tubing 200. The isolation solenoid is closed, blocking any suction to milk bottle 250 via the manifold 190. The pump 150 is pumping and applies suction to the breast shield 220 via the suction tubing 200 and the suction and milk separator device 210. The low pressure (applied suction) holds the suction and milk separator diaphragm (which acts as a check valve) closed, blocking suction to the milk tubing 230.

2. Semi Venting:
The 3-way vent solenoid 170 switches to open the vent 180 to the manifold 190 and closes the connection to the vacuum pump 150. Simultaneously, isolation solenoid 260 opens allowing suction to be applied to the milk bottle 250 and the milk tubing 230. The suction tubing 200 is at lower pressure than the milk tubing, so pressure in milk tubing 230 and milk bottle 250 drops. This step is extremely brief (~0.2 second), such that milk bottle 250 pressure drops but does not have long enough to come to equilibrium with atmosphere via vent 180. The pump 150 is blocked in, but continues to run, accumulating vacuum in vacuum cylinder 160, which is positioned between the manifold and vacuum pump.

3. Final Venting:
The isolation solenoid 260 closes. Low pressure remains in milk bottle. Vacuum from suction tubing 200 continues to vent via vent 180 and the vent solenoid 170 until the pressure rises to equilibrium with atmospheric pressure. When this occurs, the diaphragm within the suction and milk separator device 210 is no longer held closed due to low pressure in the suction tubing 200, and opens due to lower pressure in the milk bottle 250. Expressed milk is pulled through the breast shield 220 and the milk tubing 230 to the milk bottle 250. The pump 150 continues to run, accumulating vacuum in vacuum cylinder 160.

The Pumping, Semi Venting and Final Venting steps are repeated. The cycle time is typically less than 5 seconds. In a preferred embodiment, the cycle time is from about 1 to 4 seconds. In a more preferred embodiment, the cycle time is from about 0.5 to 2.0 seconds. On subsequent pumping steps, accumulated low pressure from the vacuum cylinder 160 is applied to suction tubing 200 rapidly upon switch of vent solenoid 170 to connect the manifold 190 to vacuum cylinder 160 and the pump 150. This vacuum boost functionality adds efficiency to system, as it decreases how much air must be pumped by the Vacuum Pump.

The suction and milk separator device 210 is located in immediate proximity to the breast shield 220. The suction and milk separator device exists to enforce the separation between the milk that flows into the milk tubing and the air flow from the suction tubing. It has three ports. The breast shield attaches to the larger port at the front. The suction tubing 200 attaches to a port on top, and the milk tubing 230 attaches to a port centered on the bottom. Suction pulls the milk down to be collected at the bottom of the separator device 210 where it flows through the milk tubing 230 to the milk bottle 250. A check valve or a diaphragm 211 may be in place within the separator device in order to ensure that no milk reaches the suction port on the top of the separator device 210.

The breast shield interfaces sealingly with the nipple to transfer suction to the nipple and to direct the flow of expressed milk away from the breast to the suction and milk separator device. The breast shield of the present breast pump system is designed to simulate the feel and action of a baby's mouth. The shield is made of a soft silicone rubber or plastic polymer and is designed to stimulate the nipple in a manner similar to a baby's mouth and tongue.

The use of a vacuum cylinder allows the use of a smaller, quieter pump than would otherwise be required. The pressure vessel acts as a vacuum storage reservoir. As the pump stays running throughout the cycle, the vent solenoid opens to the manifold and the pump, and closes the vent, and provides vacuum for the system. When the vent solenoid closes to the pump and the opens to the vent and the manifold, the system is vented, except for the pressure vessel, which is being further vacuumed by the continuously running pump. When the vent solenoid is closed to the vent and open to the manifold and pump, the lower pressure in the pressure vessel provides a vacuum boost to the system, even with a smaller, quieter pump, and the pump runs continuously rather than switching on and off.

The present breast pump system can be controlled wirelessly by an app on a user's smart phone or other digital device or by a front-panel display and controls. The remote app gives users the option of having very detailed control of the settings (pumping curves, detailed cycle timings, etc.), or allows simple single-slider-based control of the settings. Further, the pump system captures the detail of the volume of milk produced in a given pumping session. This data is uploaded from the app to an internet cloud service for storage, analysis and retrieval to display. The app also may track pumping duration, breastfeeding frequency and diaper changes, so multiple apps or devices are not needed.

Figure 8:
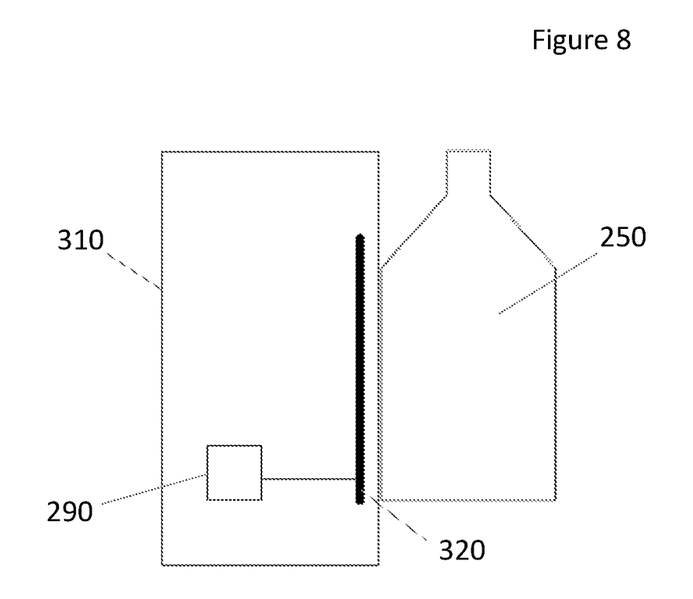
FIG. 8 is a diagram of a level sensor with the milk bottle of the present invention.

As shown in FIG. 8, a milk level sensor 320 can be used to determine the volume of milk pumped. As shown in FIG. 8, the sensor 320 is positioned inside the pump housing 310, running the height of the milk bottle. The bottle is secured so that the air gap between the bottle and the sensor is minimized. The sensor electrodes are parallel to and facing the bottle. In a preferred embodiment, there is one sensor per bottle and one bottle per breast so as to be able to track milk expression independent per breast.

An example of a preferred sensor is disclosed in US 2016/0,003,663A1, which is hereby incorporated by reference.

The microprocessor 290 is able to calculate the volume of milk expressed. In a preferred embodiment, the sensor 320 can be paired with a load cell to measure the weight of the milk expressed in order to calculate the density of the milk, yielding information about the solids content of the milk.

The pump system 100 can have custom settings entered by the user. Optional presets are provided that may be helpful to the new user. This provides new moms with a better starting point, rather than just being given a pump and told to start pumping with no other guidance. The pump is much quieter than those currently used, because a much smaller pump can be used. In a preferred embodiment, a brushless motor, rather than using a traditional diaphragm pump, is used. In another preferred embodiment, a linear pump motor that is inherently quieter is used. In another preferred embodiment, a vacuum cylinder to boost the suction is used with a pump, allowing the pump to run continually, thereby allowing a smaller (and therefore quieter) motor to be used on the pump, rather than the pump being turned on and off. The present breast pump system has the collection bottle and the pump fluidly and remotely connected to the breast shield by lengths of tubing. In a preferred embodiment, clothing and undergarments cover and engage with the shield and tubing. This provides a discreet system that can be worn under a woman's shirt.

As shown in FIGS. 4, 5 and 6, this improved product offers discretion in that women will not have to remove their shirts when breast pumping. In a preferred embodiment, the clothing that holds the breast shields are engaged with the nipple. The clothing is a three-in-one convertible undergarment. It serves the following purposes: (1) It contains the breast shield detailed below in the "comfortable" section, as well as the tubes noted above; (2) It has detachable cups similar to current nursing bras; and (3) It has built-in breast pads for when pumping is complete to prevent leaking milk from showing. These breast pads also serve as the lining of the bra.

Notice the removable cups that will allow this bra to seamlessly go from a pumping bra to a nursing bra.

Tube pathways are sewn into the bra cups. These tubes are removable for easy cleaning. The tubes dangle down the torso of the user. As noted above, one set of tubes will connect to the milk collection bottle, and the other set will connect to the vacuum pump. From the side, the bra consists of multiple pieces that are hidden in the cup of the bra. Those pieces include, outer cup bra 410, suction and milk separator device 210, breast shield 220, and removable breast pad 411.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A breast pump system to express breast milk, wherein the breast pump system comprises a suction tubing, a milk tubing, a pump, a vent valve, a suction and milk separator device, a milk bottle, an isolation valve and a breast shield;
   wherein the suction tubing has a first and second end and the milk tubing has a first and second end;
      wherein the first end of the suction tubing and the first end of the milk tubing are fluidly connected to the pump;
      wherein the second end of the suction tubing and the second end of the milk tubing are fluidly connected to the suction and milk separator device;

wherein the breast shield is fluidly connected to the suction and milk separator device, the suction tubing and the milk tubing;

wherein the suction and milk separator device has a check valve positioned at the connection to the milk tubing;

wherein the check valve has an open and a closed position and the check valve is in the closed position when the suction on the suction and milk separator device is greater than the suction on the milk tubing;

wherein the vent valve is fluidly connected to the suction tubing and is positioned between the pump and the suction and milk separator device;

wherein the vent valve is fluidly connected to a vent and the suction tubing;

wherein the milk bottle is fluidly connected on the milk tubing between the suction and milk separator device and the isolation valve; and wherein the isolation valve is fluidly connected on the milk tubing between the milk bottle and the pump.

2. The breast pump system of claim 1, wherein a vacuum cylinder is positioned between the vent valve and the pump.

3. The breast pump system of claim 2, wherein connected to the pump is a power source and a microprocessor.

4. The breast pump system of claim 3, wherein sensors generating data are positioned proximate to the milk bottle to sense the level of milk in the milk bottle;

wherein the sensors are connected to the microprocessor which stores the data.

5. The breast pump system of claim 1, wherein connected to the pump is a power source and a microprocessor.

6. The breast pump system of claim 5, wherein sensors generating data are positioned proximate to the milk bottle to sense the level of milk in the milk bottle;

wherein the sensors are connected to the microprocessor which stores the data.

7. The breast pump system of claim 6, wherein the suction tubing and the milk tubing disconnect from the three way valve, the vacuum cylinder and the pump for easy storage and cleaning.

8. A breast pump system comprising a suction tubing, a milk tubing, a pump, a vent valve, a milk bottle, and a breast shield;

wherein the suction tubing has a first and second end;

wherein the milk tubing has a first and second end;

wherein the first end of the suction tubing and the first end of the milk tubing are fluidly connected to the pump;

wherein the second end of the suction tubing and the second end of the milk tubing are fluidly connected to the breast shield;

wherein the vent valve is fluidly connected between the pump and the breast shield on the suction tubing;

wherein the milk bottle is fluidly connected on the milk tubing between the breast shield and the pump;

wherein an isolation valve is connected on the milk tubing between the milk bottle and the pump;

wherein a suction and milk separator device is fluidly connected to the second end of the suction tubing, the second end of the milk tubing and the breast shield; and wherein the second end of the milk tubing has a check valve function.

9. The breast pump system of claim 8, wherein the check valve function is a diaphragm check valve.

10. The breast pump system of claim 8, wherein a vacuum cylinder is positioned between the vent valve and the pump, and wherein the vent valve is a three way valve.

* * * * *